United States Patent [19]

Hahn

[11] Patent Number: 5,110,795
[45] Date of Patent: May 5, 1992

[54] METHODS AND COMPOSITIONS FOR THE TREATMENT OF INFLAMMATORY BOWEL DISEASES AND CONDITIONS

[75] Inventor: Gary S. Hahn, Cardiff by the Sea, Calif.

[73] Assignee: Immunetech Pharmaceuticals, San Diego, Calif.

[21] Appl. No.: 471,147

[22] Filed: Jan. 26, 1990

Related U.S. Application Data

[63] Continuation-in-part of PCT/US87/03222, Dec. 9, 1987, and a continuation-in-part of PCT/US87/03223, Dec. 9, 1987, and a continuation-in-part of Ser. No. 939,927, Dec. 9, 1986, Pat. No. 4,816,449, which is a continuation-in-part of Ser. No. 899,891, Aug. 25, 1986, abandoned, which is a continuation-in-part of Ser. No. 824,945, Feb. 3, 1986, Pat. No. 4,628,045, which is a continuation-in-part of Ser. No. 746,175, Jun. 18, 1985, abandoned, which is a continuation-in-part of Ser. No. 522,601, Aug. 12, 1983, abandoned.

[51] Int. Cl.⁵ .................. C07K 7/06; A61K 37/02
[52] U.S. Cl. .................. 514/17; 530/330
[58] Field of Search .............. 530/328, 329, 330, 331; 260/112.5 R; 514/15, 16, 17, 18

[56] References Cited

U.S. PATENT DOCUMENTS

| | | | |
|---|---|---|---|
| 4,161,522 | 7/1979 | Hamburger | 424/177 |
| 4,171,299 | 10/1979 | Hamburger | 260/112.5 R |
| 4,533,654 | 8/1985 | Lederis et al. | 514/12 |
| 4,677,120 | 6/1987 | Parish et al. | 514/549 |
| 4,693,993 | 9/1987 | Stewart et al. | 514/14 |
| 4,760,051 | 7/1988 | Pickart | 514/6 |
| 4,798,823 | 1/1989 | Witzel | 514/11 |

OTHER PUBLICATIONS

Nast et al., Chemical Abstracts, 1988, 108, 165466t.

Primary Examiner—Lester L. Lee
Assistant Examiner—Avis Davenport
Attorney, Agent, or Firm—Lyon & Lyon

[57] ABSTRACT

Methods and compositions for the treatment of inflammatory bowel diseases, chemically-induced irritation and inflammation, and other irritative or inflammatory conditions utilizing the peptide sequences Asp-Ser-Asp-Pro-Arg, Asp-Ser-Asn-Pro-Arg, or derivatives or salts thereof are disclosed.

21 Claims, 4 Drawing Sheets

METHODS AND COMPOSITIONS FOR THE TREATMENT OF INFLAMMATORY BOWEL DISEASES AND CONDITIONS

RELATED APPLICATIONS

The present invention is a continuation-in-part of International Patent Application Nos. PCT/US87/03222 and PCT/US87/03223, both filed Dec. 9, 1987 by the present inventor, which were submitted as national United States applications on Jun. 9, 1989. Each of these PCT applications is a continuation-in-part of U.S. application Ser. No. 939,927, filed Dec. 9, 1986 and now U.S. Pat. No. 4,816,449. U.S. Pat. No. 4,816,449 is a continuation-in-part of Ser. No. 899,891 (filed Aug. 25, 1986 and now abandoned) which is a continuation of Ser. No. 824,945 (filed Feb. 3, 1986, and now U.S. Pat. No. 4,628,045), which is a continuation of Ser. No. 746,175 (filed Jun. 18, 1985 and now abandoned), which is a continuation-in-part of Ser. No. 522,601 (filed Aug. 12, 1983 and now abandoned). The entire disclosures of the foregoing applications and patents are incorporated herein by reference.

BACKGROUND OF THE INVENTION

The immune system of humans and animals normally functions to protect its host from infectious organisms or from cancerous transformation by host cells. In many instances however, the immune system manifests a response that itself results in considerable damage to otherwise healthy cells and organs. Such over-reactivity of immune responsiveness is responsible for many serious conditions or diseases including allergies and autoimmune diseases.

In order to classify the processes by which the immune system produces cellular damage, immunologists have divided immune responses into four broad classes (Type I, II, III and IV) (Roitt, I. M., et al., *Immunology*, C. V. Mosby, N.Y., 1985, p. 19.1).

Type I responses are also called immediate hypersensitivity reactions and include those diseases which produce the symptoms classically associated with "allergies" or the "allergic syndrome" including allergic rhinitis (hay fever), allergic asthma, allergic conjunctivitis and allergic reactions to insect stings or foods. These conditions are characterized by a rapid clinical manifestation of allergic symptoms within minutes after exposure to an antigen (allergen) to which the subject has been previously sensitized.

In order for Type I hypersensitivity to occur, a specialized sequence of events within mast cells and basophils must be triggered by immunoglobulin E (IgE) antibodies that have been manufactured within the body. In this process, IgE directed toward an antigen (allergen) must bind to receptors on mast cells and basophils which specifically bind to the Fc region of IgE. Mast cells and basophils that have allergen-specific IgE bound to them are considered to be sensitized or "armed" for subsequent exposure to allergen. Should allergen be introduced into the local environment of the mast cells or basophils, the cells are automatically stimulated or "triggered" to release histamine and other vasoactive chemicals which produce the familiar "allergic symptoms" characteristic of allergic disease.

The hypersensitivity states characterized by types II, III and IV hypersensitivity are distinguished from type I hypersensitivity by many distinct and diverse features.

Type II hypersensitivity occurs when IgG or IgM antibodies bind to antigens located on the surfaces of cells. Such binding is mediated by the antibodies' Fab arms which contain specific structures that recognize cell surface antigens. Upon binding, the Fc regions of IgG or IgM interact with the complement system (a family of inflammatory and cell-killing molecules) or immune system "killer" cells bearing IgG or IgM Fc receptors. Some examples of diseases in which type II hypersensitivity reactions predominate include transfusion reactions, hemolytic disease of the newborn, autoimmune hemolytic anemias, hyperacute graft rejection, Goodpasture's syndrome, myesthenia gravis and other conditions.

Type III hypersensitivity is produced when complexes or aggregates of antibodies (usually IgG or IgM) and soluble antigens form in abnormally large amounts and activate the complement inflammatory system. Some examples of diseases in which type III hypersensitivity reactions are pathogenically important include systemic lupus erythematosis, rheumatoid arthritis, polyarteritis and other forms of vasculitis, fibrosing alveolitis and many infectious diseases, especially bacterial endocarditis, hepatitis and malaria.

Type IV hypersensitivity (delayed-type hypersensitivity), by contrast to the other three hypersensitivity reactions, is triggered primarily by T cells having specialized T cell receptors able to recognize and bind to the specific sensitizing antigen on a cell's surface. Upon reexposure to an antigen, T cell receptor molecules bind to the antigen and trigger a complex series of events that result in secretion of lymphokines and other regulatory molecules that recruit new cells leading ultimately to the destruction of the antigen-bearing cell. Delayed type hypersensitivity, as its name implies, has a delayed onset of inflammation that ranges from about 24 hours to several days after reexposure to the sensitizing antigen. Diseases in which type IV hypersensitivity is believed to play an important pathogenic role are frequently termed "T-cell mediated" to reflect the unique role played by the T-cell in recognizing the sensitizing antigen. These diseases include multiple sclerosis, rheumatoid arthritis, juvenile onset diabetes mellitus, ulcerative colitis, and regional enteritis (Crohn's disease), among others.

An important principle that distinguishes type I hypersensitivity (allergy) from the other hypersensitivity states discussed above is that the allergic inflammation begins within minutes after allergen exposure. By contrast, other hypersensitivity states exhibit inflammation only after hours to days following reexposure to the sensitizing agent.

A second important principle that distinguishes type I hypersensitivity from other hypersensitivity states is the source of the sensitizing agent. In type I hypersensitivity, the sensitizing agent (allergen) is not a part or component of the host body. Instead, the allergen is a substance found outside of the host body that is later introduced into the body by exposure to the environment. Types II, III and IV hypersensitivity, by contrast, may have immune responses directed towards antigens located on cells and molecules that are normal constituents of the body. Such immune responses toward normal constituents of the body are termed "autoimmune diseases" and constitute a medically important class of diseases distinct from allergic diseases.

A third important principle that distinguishes type I hypersensitivity from other hypersensitivity states is the degree to which cell killing occurs. In type I hypersensitivity, the IgE-mediated triggering reaction which causes the release of vasoactive allergic mediators does not result in the death of the releasing mast cell or basophil. Instead, the "trigger" reaction is the result of an active secretory process that may recur after a length of time. Similarly, the effect of the vasoactive allergic mediators on surrounding cells is regulatory, not cytotoxic. Allergic mediators serve to increase the permeability of small blood vessels and activate a variety of vasoregulatory and immunoregulatory processes that do not usually directly result in cell death. Types II, III and IV hypersensitivity, by contrast, have as a principal function cell killing reactions which normally lead to the destruction of infectious agents or cancer cells.

In 1975, Hamburger reported that a pentapeptide with a sequence derived from the constant domain of human IgE could inhibit a local cutaneous allergic reaction (Prausnitz-Kustner) by approximately 90% (Hamburger, R., Science 189:389, 1975; U.S. Pat. Nos. 4,171,299 and 4,161,522). This pentapeptide, Asp-Ser-Asp-Pro-Arg, is known as pentigetide. The peptide has been shown to inhibit systemic allergic disease in humans after injection by the subcutaneous route.

U.S. Pat. No. 4,628,045 describes a peptide having the amino acid sequence Asp-Ser-Glu-Pro-Arg. The peptide is an "active site" peptide which is capable of blocking immune complex binding to immunoglobulin Fc receptors. The patent also discloses particular activity of the peptide Asp-Ser-Asn-Pro-Arg in inhibiting rosette formation involving IgE Fc receptors on basophils and monocytes/macrophages. U.S. Pat. No. 4,161,522, issued Jul. 17, 1979 to Hamburger, reports that the peptide Asp-Ser-Asn-Pro-Arg exhibited activities of 5% and 6% in two trials which measured the ability of the peptide to block binding of IgE to lymphoblastoid tissue culture cells. Other peptides, including Asn-Ser-Asp-Pro-Arg and Asn-Ser-Asn-Pro-Arg were reported to exhibit lower activity, whereas the dimer [-Cys-Ala-Asn-Ser-Asn-Pro-Arg]$_2$ exhibited activity of 9% and 12%. Such peptides, including pentigetide, are stated to be useful in blocking the human allergic response.

All publications, patents and other reference materials referred to in the present specification are incorporated herein by reference.

SUMMARY OF THE INVENTION

The present invention discloses the surprising finding that pentigetide not only has antiallergic (anti-type I hypersensitivity) activity as specified by U.S. Pat. Nos. 4,161,522 and 4,171,299, but also has additional, unexpected medically useful properties as well. By contrast, the two cited patents disclose only that pentigetide has antiallergic (anti-type I hypersensitivity) activity. As will be presented in the present application, allergies or the "allergic syndrome" are medical conditions clearly distinct from the new disease applications disclosed in the present invention.

Specifically, pentigetide has a general anti-inflammatory activity in addition to its antiallergic anti-inflammatory activity. The anti-inflammatory activity described in the present invention is broad and extends to diseases and conditions other than IgE-mediated disease conditions. In particular, pentigetide has anti-inflammatory activity with respect to inflammatory bowel diseases and conditions including ulcerative colitis and regional enteritis (Crohn's disease).

Therapeutic antiallergic agents only rarely exhibit therapeutic activity in the non-allergic diseases and conditions disclosed in the present invention. For example, the commonly used therapies for allergic disease include antihistamines, cromolyn sodium, immunotherapy, alpha adrenergic agonists (vasoconstrictors), beta adrenergic agonists (bronchodialators), methylxanthine preparations (e.g., theophylline), mucolytics, expectorants and steroids. Of these therapeutics, only steroids exhibit anti-inflammatory activity in non-allergic diseases such as inflammatory bowel disease.

More specifically, pentigetide is able to suppress inflammation caused by a range of inflammatory reactions common to type II, III and IV hypersensitivity reactions which have been implicated in the pathogenesis of inflammatory bowel diseases, and inflammatory reactions produced by the application or exposure of the body or its parts to irritating or inflammation-producing agents.

This surprising discovery strongly suggests that pentigetide is useful in the treatment of a variety of non-allergic (non-type I hypersensitivity) conditions or diseases previously discussed. It additionally suggests that pentigetide is useful in treating and/or preventing inflammatory conditions not produced by an immune response to antigens, but instead by exposure of the body to noxious, irritating or otherwise harmful substances or stimuli produced by chemicals (such as formalin and IgG immune complexes and other irritating chemicals such as Vitamin A and its derivatives (retinoids, including tretinoin and related compounds)), electromagnetic irradiation (e.g., sunburn) or other agents or processes which produce irritation or inflammation.

It has also been discovered that the compound Asp-Ser-Asn-Pro-Arg, like pentigetide, has general anti-inflammatory activity as disclosed herein, and in particular is active in reducing or preventing inflammation associated with inflammatory bowel diseases such as ulcerative colitis and regional enteritis or Crohn's disease.

DETAILED DESCRIPTION

The present invention relates to the treatment of diseases or conditions not mediated by IgE using pentigetide or the compound Asp-Ser-Asn-Pro-Arg.

In addition to pentigetide and its pharmaceutically acceptable salts, substituted or otherwise derivatized forms of pentigetide and salts thereof, are also within the scope of the present invention. Preferred substituents include substituents at the amino terminus of pentigetide of the form RCO—, or R—, C-terminal substituents of the form —NH$_2$, —NHNH$_2$, —NHR or —NR$_2$ and C-terminal substituents of the form —OR, where each R is independently a linear or branched unsubstituted or substituted alkyl, alkenyl or alkynyl (either unbranched or branched, and preferably from 1 to about 8 carbons), or aryl, alkaryl, aralkyl or cycloalkyl (preferably of from about 3 to about 18 carbons), or, in the case of —NR$_2$, the R-groups are together a cyclized group forming (in attachment with the nitrogen atom) a 5–8 membered saturated hetrocyclic ring optionally containing an oxygen or nitrogen as a further ring heteroatom.

An amino-terminal acetyl substituent is a particularly preferred substituent, and propionyl, benzoyl and adamantyl —CH$_2$CO— substituents are also preferred. Amidating or esterifying carboxyl-terminal substituents formed from unsubstituted or lower alkyl-substituted amino, or from lower alkoxy or single-ring aryloxy, groups are preferred, and groups of the form —NH$_2$, —NHCH$_3$, —OCH$_3$ and —O(C$_6$H$_5$) are especially preferred. Amidating substituents are particularly preferred. Where an amidating group of the structure —NR$_2$ is to be cyclic in form, the N-morpholino heteroyclic structure is preferred. The use of such substituents on the amino and/or carboxyl terminus of the compound will tend to protect the peptide from metabolism in the in vivo environment and thereby increase the effective half-life of the compound in the body. Pharmaceutically acceptable acid or base addition salts of pentigetide and its derivatives are also contemplated herein.

Where one or more R groups is itself additionally substituted, preferred substituents include hydroxyl, amino, lower (C$_1$–C$_8$) alkoxyl, and, in the case of aromatic R groups, the foregoing substituents as well as nitro, chloro and bromo moieties. Such substituents may be used, for example, to alter bioactivity, solubility and/or biodistribution characteristics of the subject peptides. Where R includes an aryl group, substituents occurring on the meta and/or para positions (i.e., 3'- and/or 4'-positions) are most preferred. Preferred alkaryl forms of R include (3'- methyl)phenyl and (4'- methyl)phenyl groups.

Similarly, substituted or otherwise derivatized forms, such as those described immediately above, of the compound Asp-Ser-Asn-Pro-Arg are also within the scope of the present invention. Pharmaceutically acceptable salts of Asp-Ser-Asn-Pro-Arg and its derivatives are also contemplated.

Pentigetide, Asp-Ser-Asn-Pro-Arg and their derivatives as described above may be used in the treatment of various inflammatory disease conditions initiated by biological systems or pathways other than IgE. Particular examples of such non-IgE-mediated disease conditions are noted above in the discussion of Type II, III and IV hypersensitivity responses, and include a broad range of inflammatory conditions that are substantially non-allergic (non-type I hypersensitivity), i.e., non-IgE-mediated, in nature. Additional examples of such disease conditions are discussed in U.S. Pat. No. 4,628,045, the disclosure of which is incorporated herein by reference, and are contemplated to be within the scope of the present invention. Thus, inflammatory diseases which involve in substantial part non-IgE-mediated mechanisms, even if in combination with IgE-mediated mechanisms, may be expected to be inhibited or prevented to an enhanced degree by virtue of the activity of pentigetide against one or more disease-contributive non-IgE-mediated disease mechanisms.

The following examples demonstrate the utility of pentigetide and Asp-Ser-Asn-Pro-Arg in treating such non-IgE-mediated inflammatory disease conditions.

EXAMPLE 1

Pentigetide Inhibition of Type III Hypersensitivity a. Inflammatory Bowel Disease Model A mouse model of intestinal inflammation was employed wherein the efficacy of pentigetide in reducing inflammation induced by formalin and complement-fixing IgG immune complexes was measured. This model is particularly useful as a model of human ulcerative colitis and shares many clinical and histological functions of the human disease including sensitivity to glucocorticoids, sulfasalazine and 5-aminosalicylic acid (see L. P. Walsh, et al., British J. Pharm. 91:294 (1987); A. Blackham, et al., British J. Pharm. 89:694 (1986); L. D. Walsh and I. J. Zeitlin, British J. Pharm. 92:741 (1987)). The mouse model of intestinal inflammation used in these studies is induced by the exposure of the animals to chemicals which are known to trigger inflammatory processes in both animals and humans. The first step in inducing inflammation in this model is the exposure of tissues to formalin (an aqueous solution of formaldehyde gas), which is known to produce irritation and inflammation upon contact with cells of animals or humans (Clinical Toxicology of Commercial Products (R. E. Gosselin, et al., editor), 5th edition, Williams & Wilkins, 1984, pp. III-196 to III-198). At the peak of formalin-induced inflammation, IgG immune complexes are injected to further activate inflammatory processes which involve activation of leukocytes and the complement system. Inflammation induced by immune complexes is classified as Type III hypersensitivity and contributes to many disease processes, some of which were previously discussed.

In the present measurements, three trials were used: a dose-response trial, a "therapeutic"-vs.-"prophylactic" treatment trial, and a trial which compared pentigetide to Asp-Ser-Asn-Pro-Arg, control peptides and to a vehicle control solution.

In the immune complex-mediated ulcerative colitis model employed, intestinal inflammation was induced in male BKA mice (outbred swiss albino) (20–30 g) using the method described by Walsh in mice (i.e., Walsh, et al., British J. Pharm. 91:294, 1987) and by Hodgson in rabbits (Hodgson, et al., Gut 19:225 (1978)). As a primary irritant, 1% formalin in saline was instilled intra-rectally into mice. Three hours later, at the peak of the initial formalin response, immune complexes composed of polyclonal rabbit anti-human serum albumin (HSA) (Sigma) formed in antigen excess were injected i.v. The resultant colitic inflammation reached a maximum three days later. Mice were then sacrificed for evaluation.

Peptides were synthesized by the solid phase method and purified by high performance liquid chromatography. Prior to packaging, all peptides were filter sterilized using 0.22 μ filters. Packaged peptides were randomly selected and found free of endotoxin using the limulus amebocyte lysate assay (Whittaker Bioproducts).

Colonic tissue water content was determined by tissue weight loss on drying of colonic tissues. Colitic sign scores were evaluated using a single point assignment for the presence of each of the parameters listed in Table 1.

TABLE 1

Parameters Used for the Assessment of Colitis (Colitis Score)

One point assigned for the presence of each of the following parameters:

| | |
|---|---|
| Clinical symptoms of colitis: | Diarrhea |
| | Rectal hemorrhage |
| Macroscopic features of the colon: | Edema |
| | Erythema |
| | Ulceration |
| | Stricture formation |
| | Mucous |

Each experiment consisted of (A) a group of untreated healthy mice (n=10), (B) a vehicle treated control group which had received only intra-rectal formalin solution (n=10), (C) a group of formalin+IgG-anti HSA-treated mice given s.c. saline injections and (D) one or two formalin and IgG-anti HSA experimental drug treatment groups (n=10).

The response to immune complex alone was determined quantitatively by subtracting the mean value in group B from the mean value in group C. An estimate of the percentage reduction in this response produced by the drug was calculated as:

$$\text{Percentage Reduction} = 100 \cdot \frac{(\text{Group C}) - (\text{Group D})}{(\text{Group C}) - (\text{Group B})}$$

Group A animals (healthy) were used as a baseline to monitor Group B animals (formalin instillation only). Since the formalin-induced inflammation is transient, any inflammation present in the formalin only group (compared with healthy group A) at sacrifice on day 3 would constitute evidence that an unknown source of inflammation was present and all results from that particular experiment would be discarded. Statistical significance was determined using the non-parametric Mann-Whitney U-test.

b. Peptide Administration

Dose-Response Trial

In order to establish a dose-response profile for pentigetide, animals received 0.012, 0.06, 0.3, 1.5, 7.5 or 37.5 mg pentigetide/kg subcutaneously 1 day prior and 1 hour prior to induction of colitis and daily for a further 3 days until sacrificed. Vehicle control or control peptides were administered to control groups in the same volume and according to the same schedule as pentigetide. Prednisolone (5 mg/kg) was administered i.p. daily for three days prior to induction of colitis and subsequently daily for a further 3 days as a positive control.

Therapeutic-vs.-Prophylactic Trial

A "therapeutic" administration schedule was used to test whether pentigetide could suppress an ongoing inflammatory response by first injecting pentigetide after the administration of formalin and immune complexes. Therapeutically treated mice were given 1.5 mg pentigetide/kg s.c. 3 hours post-immune complex (6 hours post-formalin) and daily thereafter.

A second "prophylactic" treatment regimen was used to determine whether pentigetide could suppress inflammation if injected immediately prior to immune complex administration. In this study, 1.5 mg/kg pentigetide was first injected s.c. 1 hour prior to intra-rectal formalin and daily thereafter. Prednisolone (5.0 mg/kg) was used as a positive control and injected i.p. 3 days, 2 days, and 1 day prior to, and on the day of, formalin and immune complex administration and then daily thereafter for three days.

Control Peptide and Asp-Ser-Asn-Pro-Arg Trial

In these experiments, mice were treated with one of the following peptide or vehicle control solutions A, B, C, D or E:

A Pentigetide (Asp-Ser-Asp-Pro-Arg [DSDPR])
B Asp-Ser-Asn-Pro-Srg (DSNPR)
C Phosphate buffered saline
D A scrambled pentigetide sequence (Asp-Pro-Asp-Arg-Ser [DPDRS])
E A second control peptide (Pro-Ser-Lys-Gly-Thr [PSKGT]) unrelated to pentigetide A dose of 0.3 mg/kg of each peptide was used. As in the dose-response trial, solutions were administered s.c. 1 day prior to and 1 hour prior to induction of colitis and daily for a further 3 days until animals were sacrificed.

c. Results

Figure 1A:
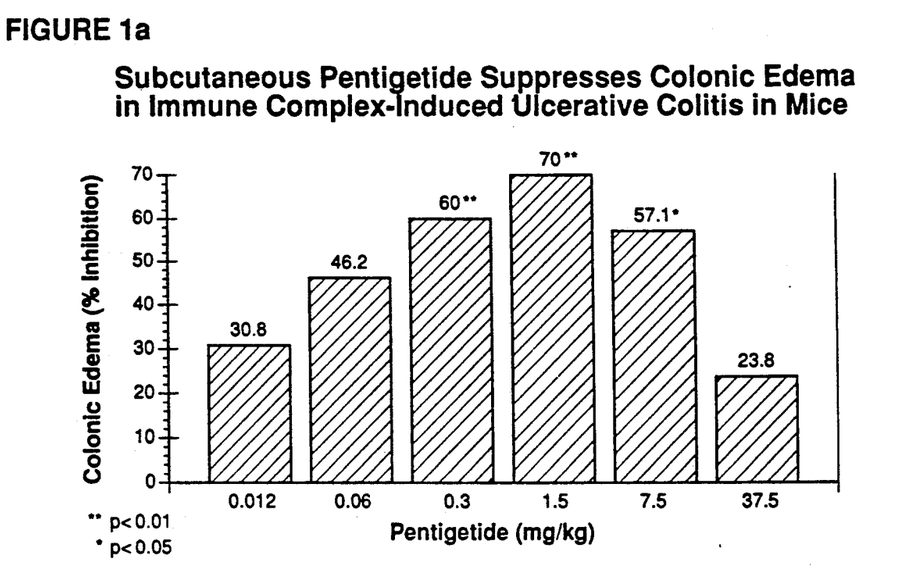
FIGS. 1a and 1b depict the inhibition of colonic edema and colitic signs in mice as a function of dosage of the peptide Asp-Ser-Asp-Pro-Arg.
Figure 1B:
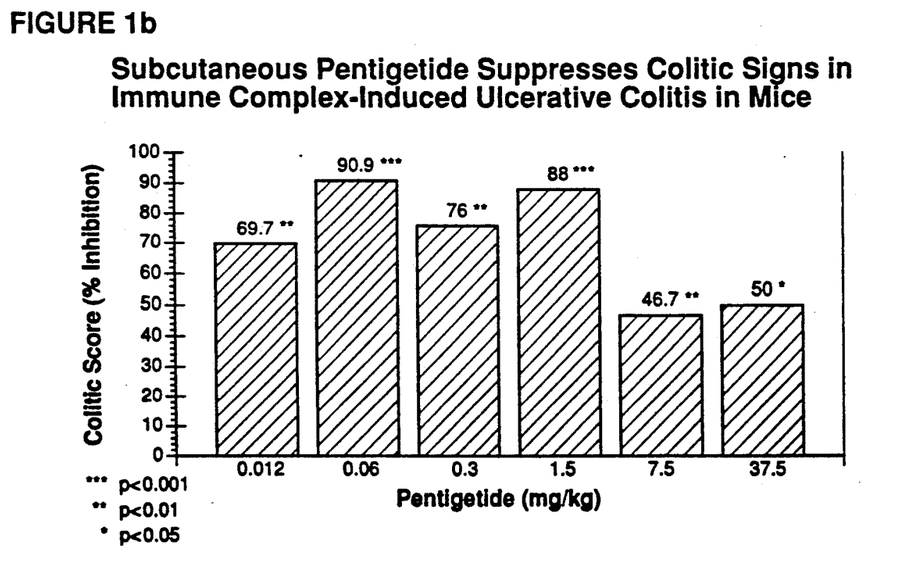

Dose Response Trial: FIGS. 1a and 1b

FIG. 1a shows percent inhibition of colonic edema in mice treated with increasing doses of pentigetide. A trend of increasing inhibition with increasing dose is evident with statistically significant inhibition (60.0%, p<0.01) first observed at 0.3 mg/kg. The maximum inhibitory response to pentigetide (70.0%, p<0.01) was observed at 1.5 mg/kg. Above this dose, the drug was decreasingly effective in reducing the edema response.

Data derived from the colitic score reveals a similar dose-response pattern (FIG. 1b). A significant reduction in colitic signs was produced at every dose tested. Even the lowest dose tested (0.012 mg/kg) produced a large reduction (69.7%, p<0.01) in the mean colitis score. Pentigetide was maximally effective at concentrations of 0.06 mg/kg (90.9%, p<0.001), 0.3 mg/kg (76.0%, p<0.01) and 1.5 mg/kg (88.0%, p<0.001). As noted with the edema response, above 1.5 mg/kg the drug was decreasingly effective in suppressing the signs of colitis.

Figure 2A:
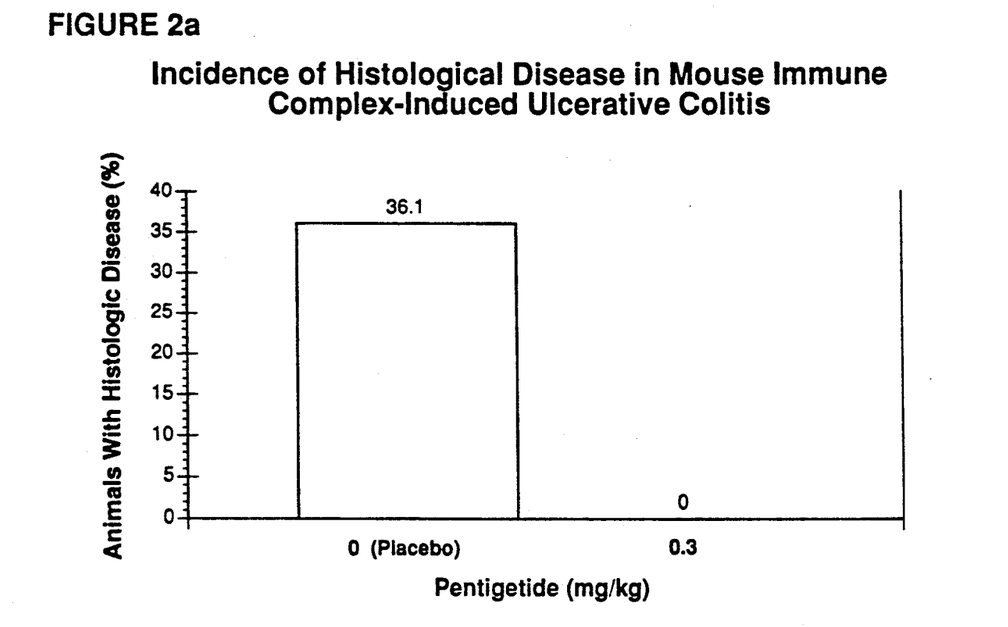
FIGS. 2a and 2b depict the inhibition by Asp-Ser-Asp-Pro-Arg of microscopic evidence of inflammation in mice in an immune complex-induced ulcerative colitis model.
Figure 2B:
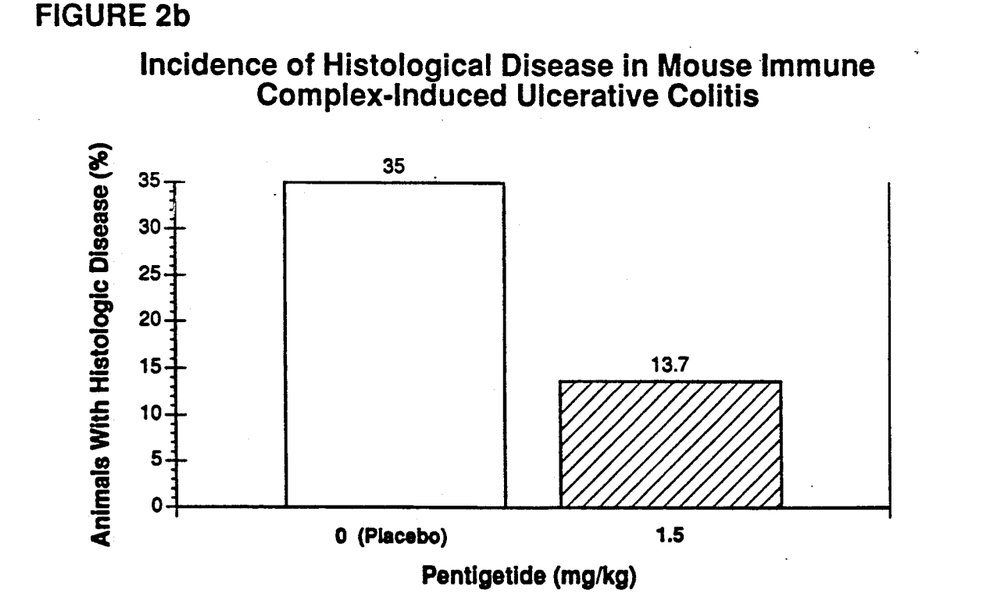

Microscopic Analysis of Therapeutic and Peptide Control Trial: FIGS. 2a and 2b

Microscopic analysis of hematoxylin and eosin-stained slides of colonic tissues from pentigetide or saline-treated mice demonstrate that pentigetide reduced the incidence of inflammatory changes in the colon. In the studies of pentigetide-treated mice receiving 0.3 mg/kg, no inflammatory changes were observed while 36.1% of the vehicle control-treated mice exhibited microscopic signs of colon inflammation which include edema, leukocytic infiltration, mucosal atrophy, fibrosis, hemorrhage, lumenal cellular debris, necrosis and ulceration (FIG. 2a).

A similar reduction of microscopic lesions was observed in mice treated with 1.5 mg/kg (FIG. 2b). Of the vehicle control-treated mice, 35.0% had significant microscopic lesions while 13.7% of pentigetide-treated mice had lesions.

Figure 3A:
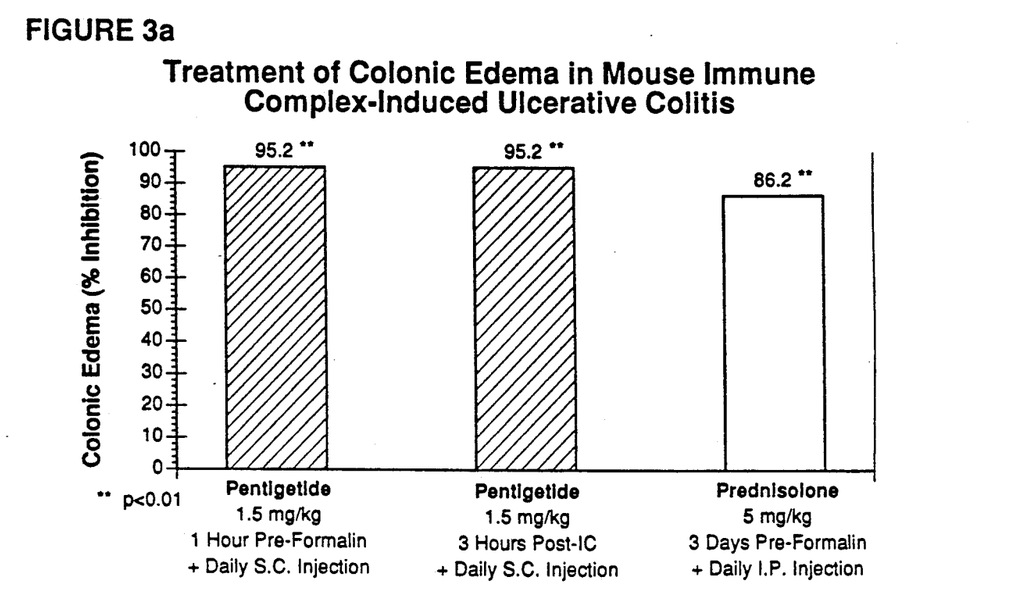
FIGS. 3a and 3b compare the inhibition by Asp-Ser-Asp-Pro-Arg and prednisolone of colonic edema and colitic signs in mice treated with Asp-Ser-Asp-Pro-Arg immediately prior to or after inflammation induction in an immune complex-induced ulcerative colitis model.
Figure 3B:
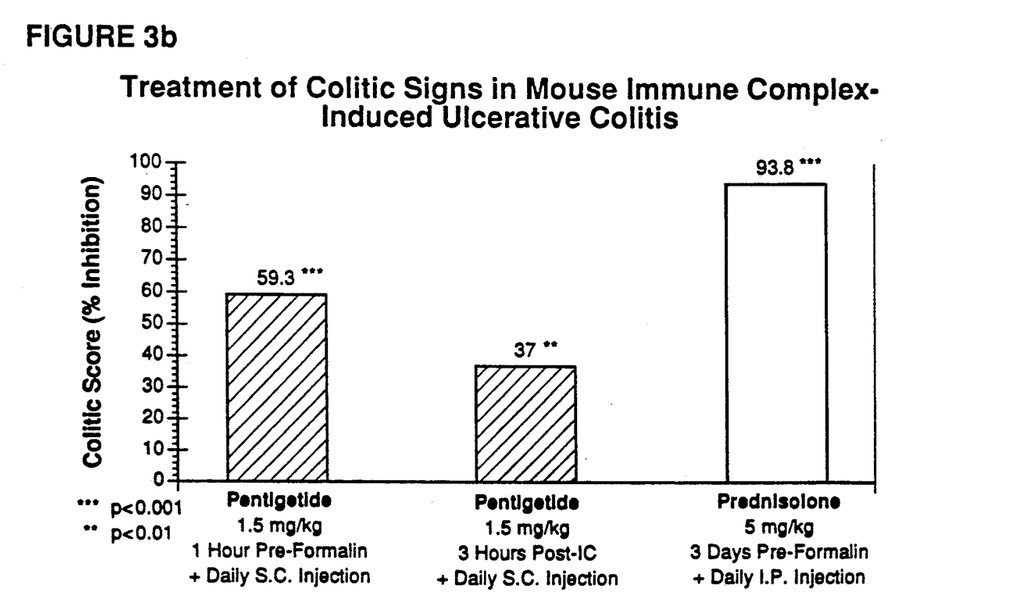

Therapeutic Trial: FIGS. 3a and 3b

Pentigetide treatment (1.5 mg/kg) commencing either one hour prior to the initial induction of inflammation (intrarectal formalin instillation) or three hours after the administration of i.v. immune complexes (six hours after intrarectal formalin instillation) resulted in substantial and statistically significant reduction of colonic edema (FIG. 3a). Both dosing regimens resulted in an identical reduction of colonic edema (95.2%, $p<0.01$). Mice receiving i.p. injections of prednisolone (5.0 mg/kg) for three days prior to inflammation induction and then daily thereafter experienced a comparable reduction of colonic edema (86.2%, $p<0.01$).

The colitic sign scores of these mice were also suppressed for both dosing regimens when compared to saline-treated control mice (FIG. 3b). "Prophylactic" pentigetide treatment commencing one hour prior to formalin-administration resulted in a 59.3% ($p<0.001$) reduction of the colitic score while "therapeutic" pentigetide treatment resulted in a 37.0% ($p<0.01$) reduction of the colitic score. Prednisolone-treated mice experienced a 93.8% ($p<0.001$) reduction of colonic edema.

Figure 4A:
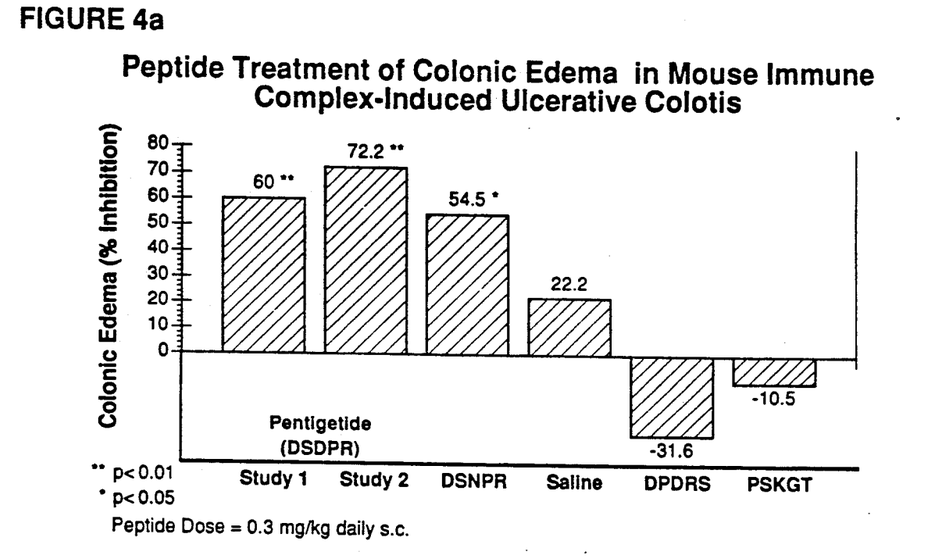
FIGS. 4a and 4b depict the inhibition by Asp-Ser-Asp-Pro-Arg (DSDPR), Asp-Ser-Asn-Pro-Arg (DSNPR) and control peptides (DPDRS and PSKGT) of colonic edema and colitis signs in mice in an immune complex-induced ulcerative colitis model.
Figure 4B:
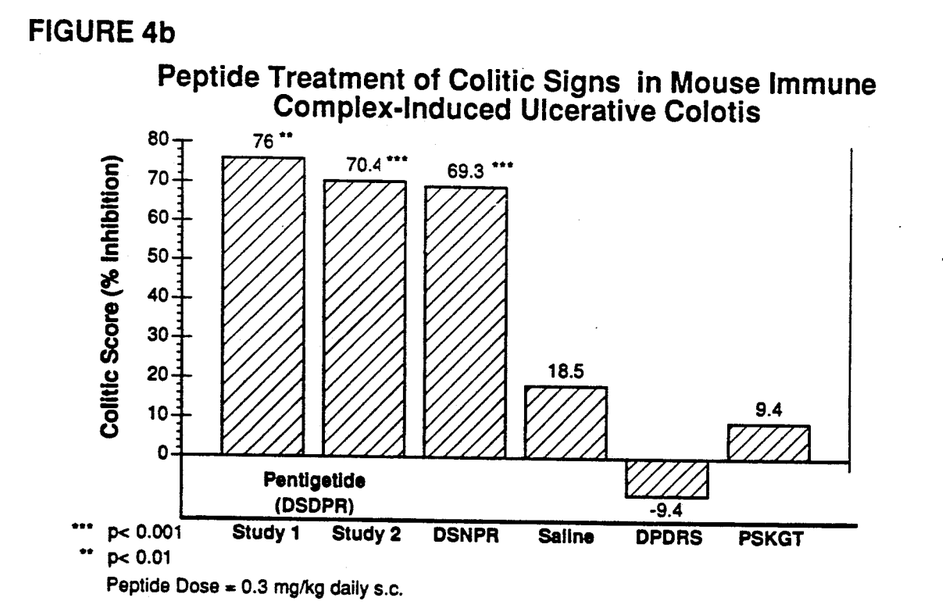

Control Peptide and Asp-Ser-Asn-Pro-Arg
Trial: FIGS. 4a and 4b

FIG. 4 illustrates the percent inhibition of colonic edema for pentigetide, Asp-Ser-Asn-Pro-Arg and two peptide controls (Asp-Pro-Asp-Arg-Ser and Pro-Ser-Lys-Gly-Thr) and saline. Only the pentigetide and Asp-Ser-Asn-Pro-Arg treated animals showed significantly reduced colonic edema with 72.2% ($p<0.01$) inhibition, and 54.5% ($p<0.05$) inhibition, respectively. This inhibition was similar to the 60.0% ($p<0.01$) inhibition observed in the first dose-response trial for the 0.3 mg/kg pentigetide dose.

Colitic sign scores, shown in FIG. 4b, were also significantly reduced only for those animals treated with pentigetide or Asp-Ser-Asn-Pro-Arg. Pentigetide produced 70.4% ($p<0.001$) suppression and Asp-Ser-Asn-Pro-Arg produced 69.3% ($p<0.001$) suppression. Neither of the two control peptides nor saline produced significant suppression of either edema or colitic score.

d. Conclusions

These studies demonstrate that pentigetide has a potent action in reducing objective and clinically-related signs of intestinal and rectal inflammation in a mouse model of inflammatory bowel disease (ulcerative colitis).

Pentigetide may be used as a prophylactic treatment to suppress disease when administered before the initiation of intestinal inflammation. Additionally, pentigetide treatment can be used as a therapeutic treatment to suppress inflammation after it has been initiated by a disease process.

The demonstrated antiinflammatory activity of pentigetide and the peptide Asp-Ser-Asn-Pro-Arg is related to the specific amino acid sequences of the respective peptide. Control peptides which resemble both pentigetide and Asp-Ser-Asn-Pro-Arg were inactive in these studies.

The fact that pentigetide and the peptide Asp-Ser-Asn-Pro-Arg can suppress inflammation caused by exposure to an inflammatory chemical like formalin in conjunction with immune complex-induced inflammation suggests that pentigetide and Asp-Ser-Asn-Pro-Arg may be therapeutically used to treat irritation and inflammation, particularly that of intestinal and rectal tissues, produced by either chemical exposure and/or by diseases or processes in which immune complexes and/or complement contribute to inflammation. In addition, the utility of the present compounds in treating intestinal and rectal inflammation suggests that inflammation produced by other processes, including but not limited to rectal inflammation associated with hemorrhoids and skin inflammation associated with exposure to chemical irritants such as, for example, Vitamin A and its derivatives (retinoids, including tretinoin and related compounds), may also be treated and/or prevented using pentigetide and the other compounds disclosed herein.

In the practice of the methods of the present invention, an effective amount of pentigetide, Asp-Ser-Asn-Pro-Arg or a derivative and/or thereof, or a pharmaceutical composition containing the same, as exemplified below, is administered via any of the usual and acceptable methods known in the art, either singly or in combination with another compound or compounds of the present invention or other pharmaceutical agents such as antihistamines, corticosteroids, and the like. These compounds or compositions may thus be administered rectally (e.g., by suppository, foam, liquid, ointment or cream), orally, sublingually, topically (e.g., on the skin or in the eyes), parenterally (e.g., intramuscularly, intravenously, subcutaneously or intradermally), or by inhalation, and in the form of either solid, liquid or gaseous dosage including tablets, suspensions, and aerosols as discussed in more detail hereinafter. The administration can be conducted in single unit dosage form with continuous therapy or in single dose therapy ad libitum. Administration may also be conducted in the course of a preventive treatment by application of a formulation containing both a compound of the invention and a second substance which may, itself, be a potential source of irritation, as for example a cosmetics substance or a topical skin formulation containing a Vitamin A (retinoid) substance.

In one preferred embodiment, the treatment method of the present invention is practiced in a "therapeutic" manner when the relief of symptoms is specifically required or perhaps imminent; in another preferred embodiment, the method hereof is effectively practiced as continuous or "prophylactic" treatment.

In view of the foregoing as well as in consideration of the degree of severity of the condition being treated, age of subject, and so forth, all of which factors being determinable by routine experimentation by one skilled in the art, the effective dosage in accordance herewith can vary over a wide range. A preferred dosage in humans, depending on the disease in question and the mode and schedule of administration, may vary from about 0.1 to 10 mg/kg, or more particularly 0.3 to 1.5 mg/kg, while a possible range of necessary doses may vary from about 1 μg/kg to 800 mg/kg.

Useful pharmaceutical or other carriers for the preparation of the compositions or medicaments hereof, can be solids, liquids or gases; thus, the compositions can take the form of tablets, pills, capsules, powders, suppositories, enterically coated or other protected formulations (such as binding on ion exchange resins or other carriers, or packaging in lipid protein vesicles) sustained release formulations solutions (e.g., ophthalmic drops), suspensions, elixirs, aerosols, creams, ointments, cosmetics preparations and the like. The carrier can be selected from the various oils including those of petroleum, animal, vegetable or synthetic origin, for example, peanut oil, soybean oil, mineral oil, sesame oil, and the like. Water, saline, aqueous dextrose, and glycols are preferred liquid carriers, particularly (when isotonic) for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in "Remington's Pharmaceutical Sciences" by E. W. Martin. Such compositions will, in any event, contain an effective amount of the active compound together with a suitable amount of carrier so as to prepare the proper dosage form for proper administration to the host.

To be effective for the prevention or treatment of inflammatory diseases it is important that the pentigetide or Asp-Ser-Asn-Pro-Arg compound be relatively non-toxic, non-antigenic and non-irritating at the levels in actual use.

The present pentigetide and Asp-Ser-Asn-Pro-Arg compounds may be synthesized by the solid phase peptide synthesis method, as described for example in Merrifield, J. Am. Chem. Soc., 85, 2149-2154 (1963); Meienhofer in "Hormonal Proteins and Peptides," ed. C. H. Li, Vol. 2 (Academic Press, 1973), pp. 48-267; and Barany and Merrifield in "The Peptides," eds. E. Gross and J. Meienhofer, Vol. 2 (Academic Press, 1980), pp. 3-285.

Exemplary solid phase methods for synthesizing such compounds are given in U.S. patent application Ser. No. 939,927, now U.S. Pat. No. 4,816,449, and are not repeated here. In particular, methods for preparation of substituted compounds as disclosed herein are also given in that patent.

It is understood that various other modifications will be apparent to and can readily be made by those skilled in the art without departing from the scope and spirit of this invention. Accordingly, it is not intended that the scope of the claims appended hereto be limited to the description as set forth above, but rather that the claims be construed as encompassing all the features of patentable novelty which reside in the present invention, including all features which would be treated as equivalents thereof by those skilled in the art to which this invention pertains.

I claim:

1. A method for the treatment of an inflammatory bowel disease comprising administering to a mammalian subject a therapeutically effective amount of a peptide, or a pharmaceutically acceptable salt thereof said peptide, having the amino acid sequence Asp-Ser-Asp-Pro-Arg.

2. A method for the treatment of an inflammatory bowel disease comprising administering to a mammalian subject a therapeutically effective amount of a derivatized peptide, or a pharmaceutically acceptable salt thereof said derivatized peptide, comprising the amino acid sequence Asp-Ser-Asp-Pro-Arg and a pharmaceutically acceptable substituent selected from $N^\alpha$-substituents of the form RCO— and R—, and C-terminal substituents of the form —NH$_2$, —NHNH$_2$, —NHR, —NR$_2$ and —OR (where each R is independently selected from unbranched and branched, unsubstituted and substituted lower alkyl, alkenyl and alkynyl groups of from 1 to about 8 carbons, aryl, alkaryl, aralkyl and cycloalkyl groups of from about 3 to about 18 carbons, and, in the case of —NR$_2$, from cyclized groups forming (in attachment with the nitrogen atom) a 5-8 membered saturated heterocyclic ring optionally containing an oxygen or nitrogen as a further ring heteroatom).

3. The method of claim 2 wherein said RCO-substituent is an acetyl substituent.

4. The method of claim 1, 2 or 3 wherein said inflammatory bowel disease is ulcerative colitis.

5. The method of claim 1, 2 or 3 wherein said inflammatory bowel disease is regional enteritis.

6. A pharmaceutical composition for the treatment of an inflammatory bowel disease comprising a pharmaceutically effective amount of a peptide or peptide salt of claim 1, 2 or 3.

7. A method for the treatment of an inflammatory bowel disease comprising administering to a mammalian subject a therapeutically effective amount of a peptide, or a pharmaceutically acceptable salt thereof said peptide, having the amino acid sequence Asp-Ser-Asn-Pro-Arg.

8. A method for the treatment of an inflammatory bowel disease comprising administering to a mammalian subject a therapeutically effective amount of a derivatized peptide, or pharmaceutically acceptable salt thereof said derivatized peptide, comprising the amino acid sequence Asp-Ser-Asn-Pro-Arg and a pharmaceutically acceptable substituent selected from $N^\alpha$-substituents of the form RCO— and R—, and C-terminal substituents of the form —NH$_2$, —NHNH$_2$, —NHR, —NR$_2$ and —OR (where each R is independently selected from unbranched and branched unsubstituted and substituted lower alkyl, alkenyl and alkynyl groups of from 1 to about 8 carbons, aryl, alkaryl, aralkyl and cycloalkyl groups of from about 3 to about 18 carbons, and, in the case of —NR$_2$, from cyclized groups forming (in attachment with the nitrogen atom) a 5-8 membered saturated heterocyclic ring optionally containing an oxygen or nitrogen as a further ring heteroatom).

9. The method of claim 8 wherein said RCO-substituent is an acetyl substituent.

10. The method of claim 7, 8 or 9 wherein said inflammatory bowel disease is ulcerative colitis.

11. The method of claim 7, 8 or 9 wherein said inflammatory bowel disease is regional enteritis.

12. A pharmaceutical composition for the treatment of an inflammatory bowel disease comprising a pharmaceutically effective amount of a peptide or peptide salt of claim 7, 8 or 9.

13. A method for the treatment of chemically-induced irritation or inflammation comprising administering to a mammalian subject a therapeutically effective amount of a peptide or peptide salt of claim 1, 2, 3, 7, 8 or 9.

14. A pharmaceutical composition for the treatment of a chemically-induced irritation or inflammation condition comprising a pharmaceutically effective amount of a peptide or peptide salt of claim 1, 2, 3, 7, 8 or 9.

15. The method of claim 13 wherein said irritation or inflammation is associated with topical exposure to a retinoid substance.

16. The pharmaceutical composition of claim 14 wherein said irritation or inflammation is associated with topical exposure to a retinoid substance.

17. A pharmaceutical composition comprising a peptide or peptide salt of claim 1, 2, 3, 7, 8 or 9 and a retinoid substance.

18. A method for the treatment of irritation or inflammation of the intestine comprising administering to a mammalian subject a therapeutically effective amount of a peptide or peptide salt of claim 1, 2, 3, 7, 8 or 9.

19. A pharmaceutical composition for the treatment of irritation or inflammation of the intestine comprising a pharmaceutically effective amount of a peptide or peptide salt of claim 1, 2, 3, 7, 8 or 9.

20. The method of claim 18 wherein said irritation or inflammation is associated with hemorrhoids.

21. The pharmaceutical composition of claim 19 wherein said irritation or inflammation is associated with hemorrhoids.

* * * * *